United States Patent [19]
Rothfuss et al.

[11] Patent Number: 5,246,156
[45] Date of Patent: Sep. 21, 1993

[54] MULTIPLE FIRE ENDOSCOPIC STAPLING MECHANISM

[75] Inventors: Robert G. Rothfuss, Bellevue, Ky.; Livyn O. Okorocha, Cincinnati, Ohio; Gregory D. Bishop, Hamilton, Ohio; Narinderjit S. Sambi, Maineville, Ohio; James J. Bedi, Cincinnati, Ohio; Salvatore Privitera, Sharonville, Ohio; Michael Sherrill, Cincinnati, Ohio

[73] Assignee: Ethicon, Inc., Somerville, N.J.

[21] Appl. No.: 759,014

[22] Filed: Sep. 12, 1991

[51] Int. Cl.⁵ .............................. A61B 17/068
[52] U.S. Cl. .................... 227/176; 227/177; 227/19
[58] Field of Search ............... 227/19, 176, 177

[56] References Cited

U.S. PATENT DOCUMENTS

| | | | |
|---|---|---|---|
| 4,127,227 | 11/1978 | Green | 227/19 X |
| 4,485,953 | 12/1984 | Rothfuss | 227/19 |
| 4,496,090 | 1/1985 | Crevier et al. | 227/19 |
| 4,592,498 | 6/1986 | Braun et al. | 227/19 |
| 4,607,638 | 8/1986 | Crainich | 411/472 X |
| 4,634,035 | 1/1987 | Li et al. | 227/19 |
| 4,664,305 | 5/1987 | Blake, III et al. | 227/19 |
| 4,787,387 | 11/1988 | Burbank, III et al. | 227/176 |
| 4,951,860 | 8/1990 | Peters et al. | 227/19 X |

Primary Examiner—Frank T. Yost
Assistant Examiner—Rinaldi Rada
Attorney, Agent, or Firm—Paul A. Coletti

[57] ABSTRACT

A unique hernia repair stapler is described which allows the forming of staples to attach prosthetics to tissue, or to approximate herniated tissue. The staple is useful in endoscopic operations and may be rotatable or stationary. The stapler has a unique forming and ejecting mechanism; as well, there is the availability of a loading mechanism useful for both cartridges and magazines of staples. An improved staple shape allows for better staple alignment, especially in a multiple load device.

13 Claims, 13 Drawing Sheets

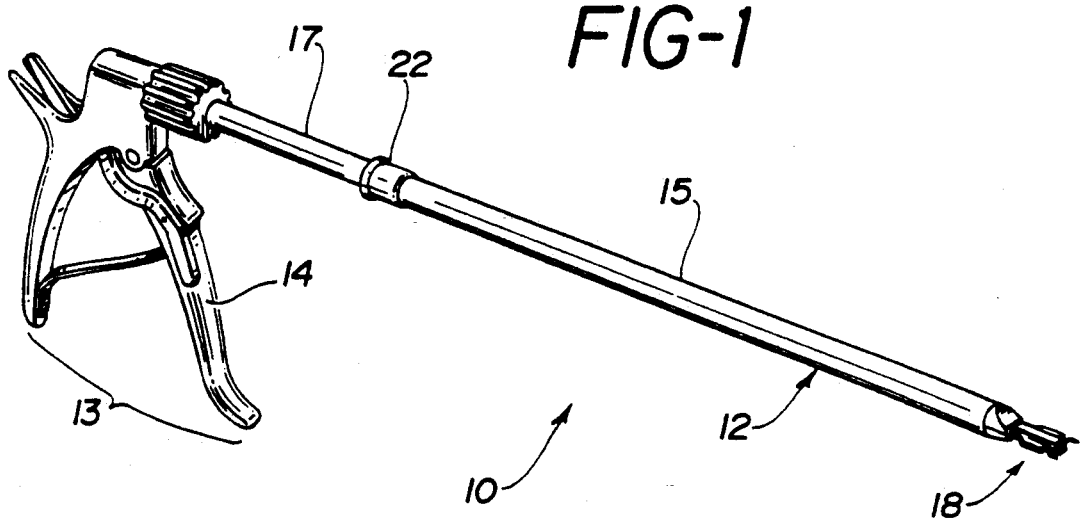
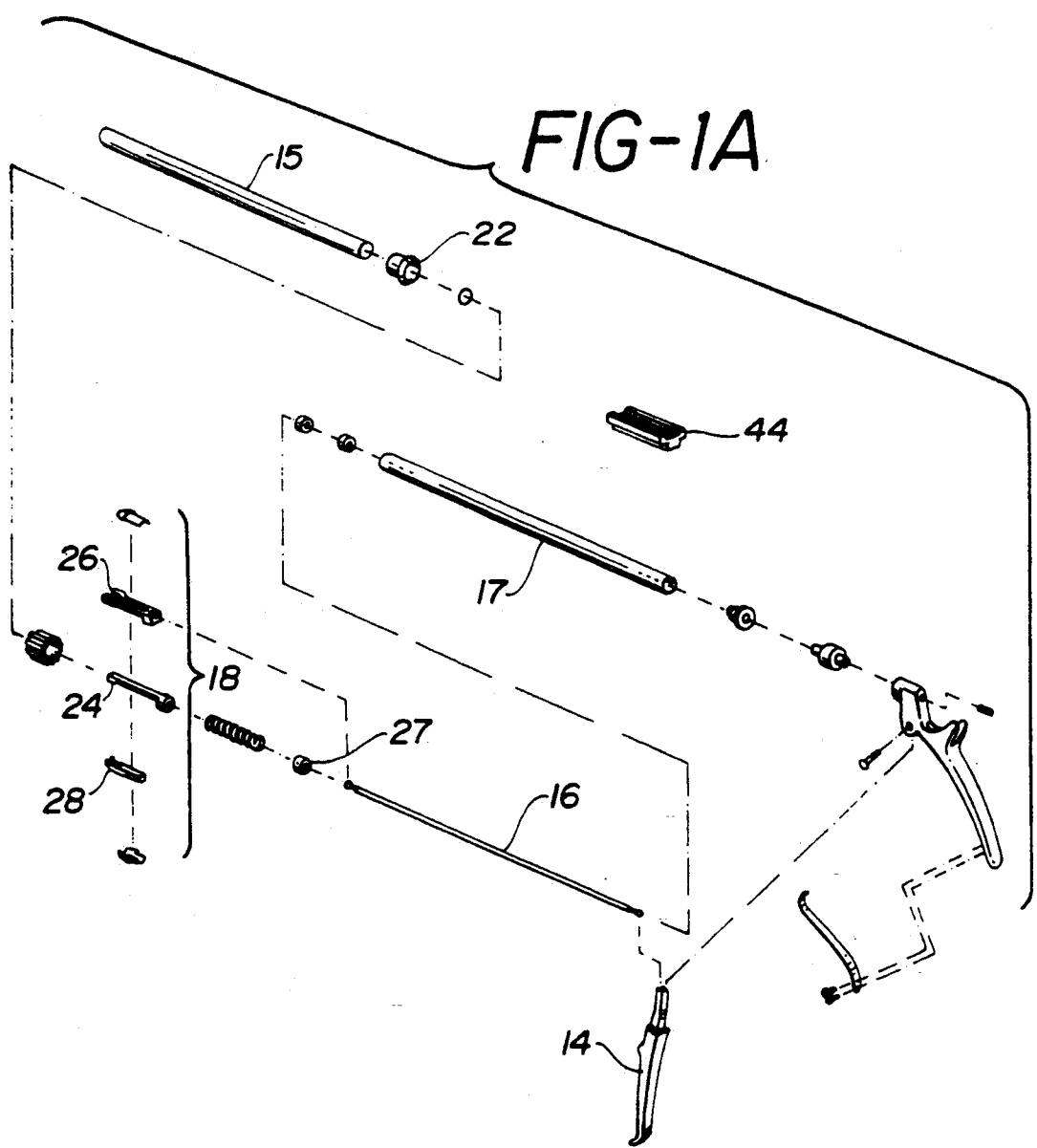

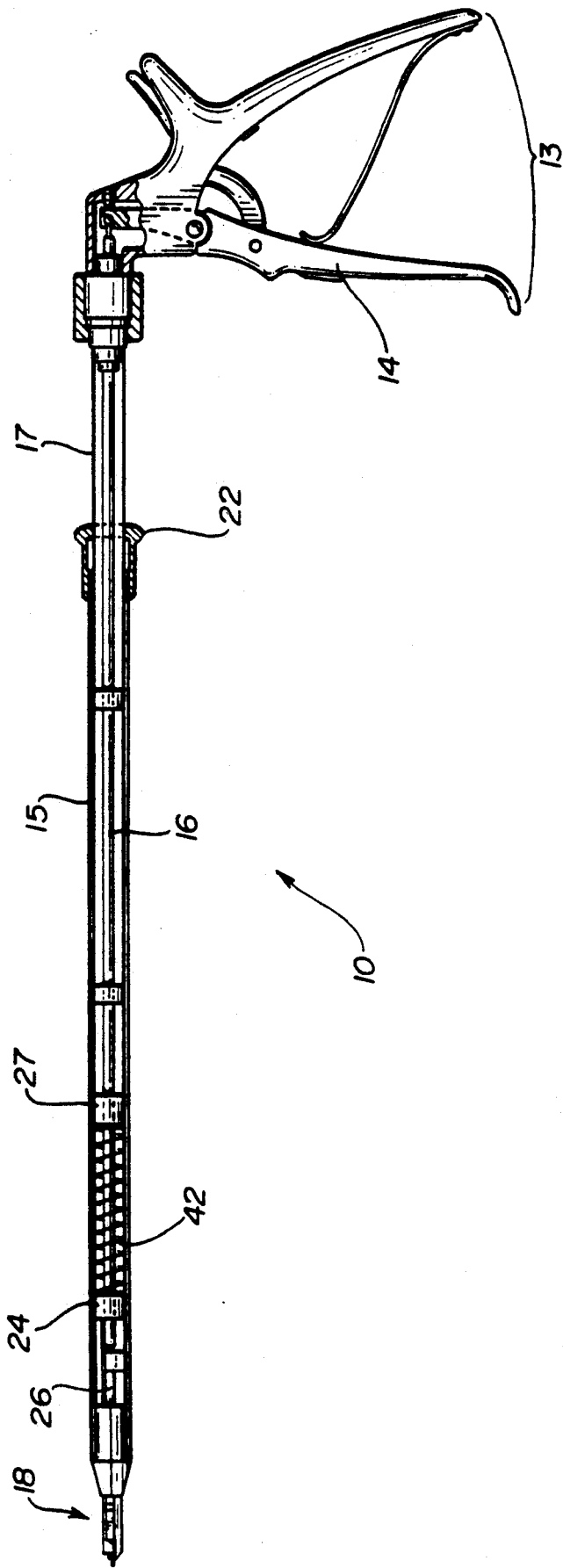

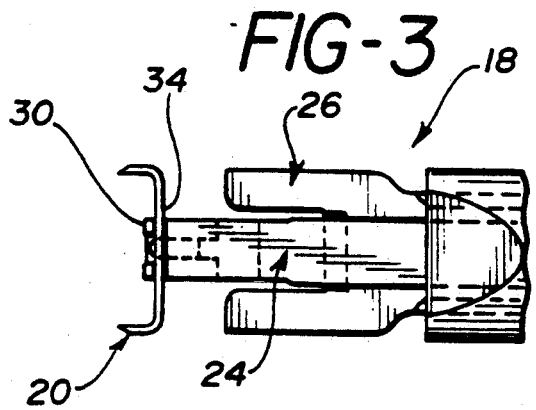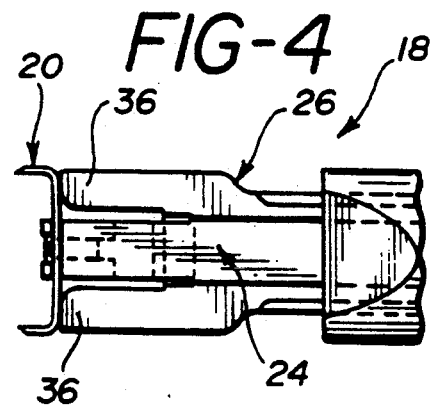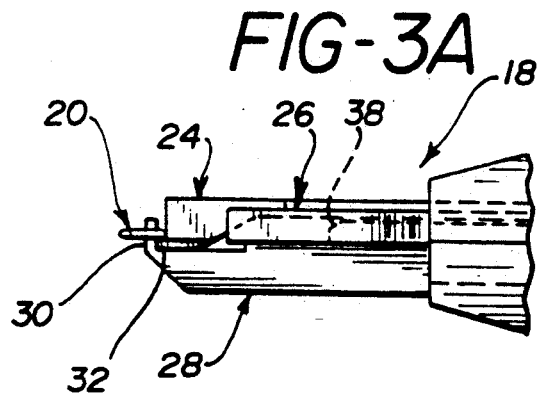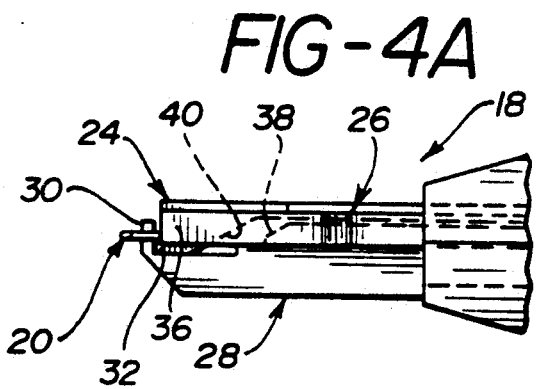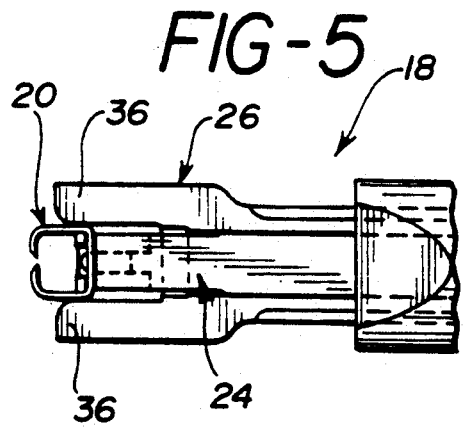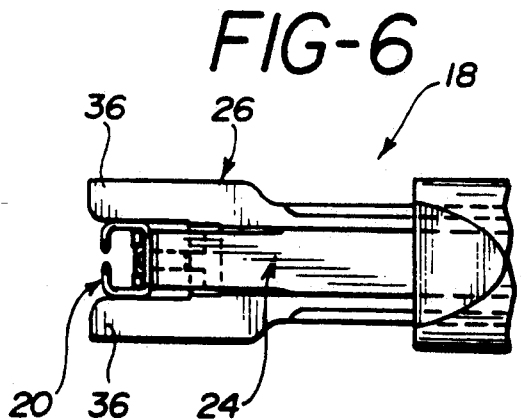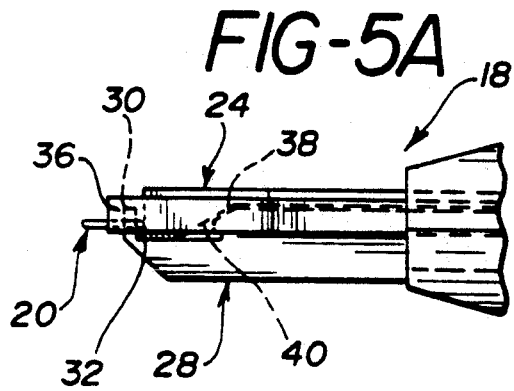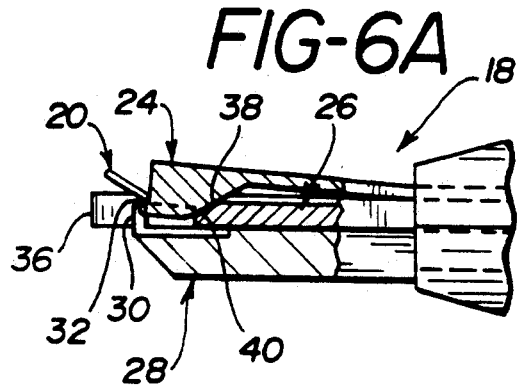

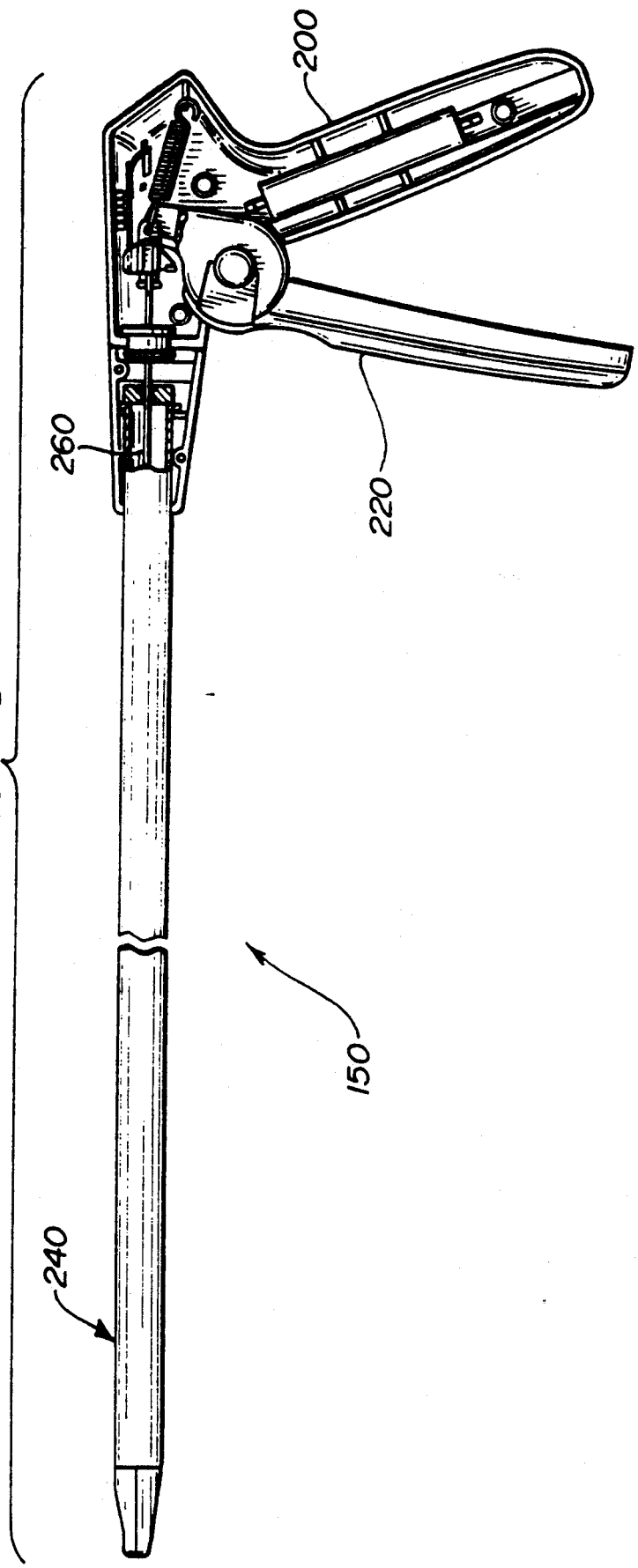

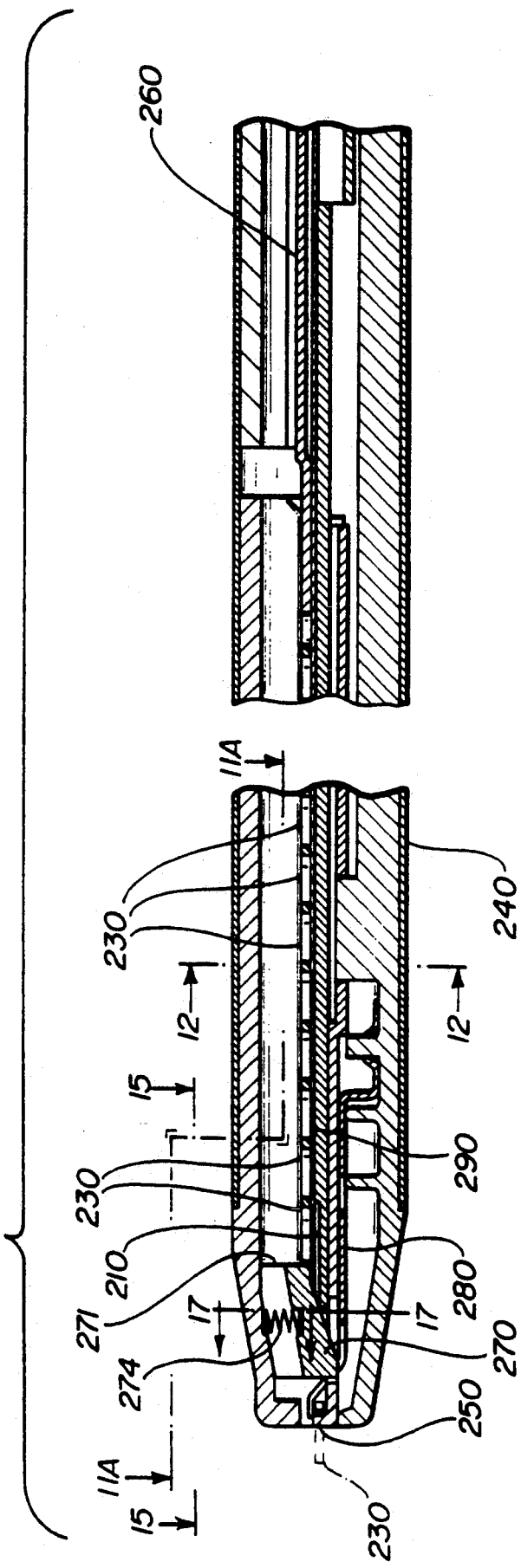

MULTIPLE FIRE ENDOSCOPIC STAPLING MECHANISM

FIELD OF THE INVENTION

Generally, this invention relates to repair mechanisms to be used endoscopically. More specifically, this invention relates to repair mechanisms which allow for the repair of hernias. Most specifically, this invention relates to a hernia repair mechanism which describes a unique stapling mechanism for endoscopically fastening a prosthetic patch over a hernia, as well as a unique loading and alignment system for use with this repair mechanism, as well as the application of metallic staples for the endoscopic approximation of herniated tissue.

BACKGROUND OF THE INVENTION

With the proliferation of endoscopic surgery, it has been realized that there are many procedures typically performed in open surgery which are now capable of being performed endoscopically. A trocar, which is a pointed piercing device, is sent into the body with a cannula placed around the trocar. After the trocar accomplishes piercing of the abdominal walls, it is removed and the cannula remains in the body. Through this cannula, endoscopic procedures are possible. Generally, these endoscopic procedures take place under insufflation. Some of the more typical procedures have been gall bladder removal, tissue repair and sterilization procedures such as occluding of the Fallopian tubes.

Surgeons realize that it may be possible to perform additional procedures endoscopically, once the proper materials and mechanisms become available for performing these procedures. One of the more basic, and quite logical extensions of current endoscopic procedures has been focused on repair of hernias. It is realized that to have the capability of performing hernia repair endoscopically will serve the medical community in many ways. Specifically, it is realized that endoscopic hernia repair will allow the patient to recuperate more rapidly, and without the more than likely extensive physical therapy currently practiced as a result of such "simple" procedures.

Moreover, it is realized that hernia repair procedures may contain aspects which are applicable in other procedures. For instance, if it is possible to cover, or reinforce and constrain a hernia it may be possible to apply this procedure to other vessels or organs, in much the similar manner. Also, it is realized that once a device becomes available wherein hernias can be repaired, many of these funtional components on these devices would be useful in other devices capable of performing other procedures. Also, naturally, these mechanisms may be useful on procedures wherein open surgery is performed.

SUMMARY OF THE INVENTION

Therefore, it is an object of the invention to provide a hernia repair device.

It is yet another object of the invention to provide a device for the permanent approximation of tissue using metal fasteners, and, specifically a hernia repair device where hernia repair can be accomplished endoscopically.

It is yet another object of the invention to provide a hernia repair device wherein mesh or prosthetic device can be applied about the hernia so that the hernia is permanently covered, in order to constrain internal organs such as the intestines.

It is yet another object of the device of the invention to provide a device which is capable of sealing or approximating tissues in much the same way as mesh is applied over the hernia.

Another object of the invention is to provide a hernia repair device which is capable of applying staples to tissues with improved staple alignment mechanisms, as well as with improved loading and ejecting mechanisms. In addition, it is perceived that such a mechanism may be capable of a multiple-load feature.

An additional object of this invention is to provide a unique staple configuration for use with a hernia repair mechanism.

A final object of the invention is to provide a reliable feed mechanism to a multiple load surgical stapler.

As a result of this invention, a hernia repair device is disclosed where the device is capable of attaching a prosthetic over the herniated tissue. The device holds and forms a staple in place so that the herniated tissue is secured and clamped. The mechanism accomplishes this procedure endoscopically, through a trocar tube. Of course, the mechanism is capable of applying the staple directly to tissue without a prosthetic wrap. The stapler is currently perceived as a single fire device, but may be converted quite readily into a multiple load mechanism.

Importantly, the stapler has a unique loading, forming and ejecting mechanism. Three parts of the mechanism are designed to slide one upon the other in order to provide the sequence of operations necessary to place the staple. The anvil portion of the stapler is the stationary reference, upon which a staple former slides upon the anvil; a staple holder slides upon the former. The staple holder is spring biased against the staple former, so that a biasing force is exerted by the holder against the anvil portion of the instrument. The spring which biases the former to the holder is also a trigger return, eliminating the need for an external spring on the device. With this biasing force, a staple may be securely loaded from either a cartridge or a magazine into the instrument. The staple holder holds the staple by use of this biasing force against the stapler anvil.

As the instrument is fired, the staple former exerts a forming motion against the staple such that it is clamped about either tissue or mesh. As the staple is formed, the staple former comes into direct contact with a camming surface on the staple holder. This camming force causes the staple holder to eject the staple from the anvil after it has been formed. Ejection is accomplished without any twisting motion of the surgeon's wrist, as is currently accomplished with some staplers. Release of the instrument trigger causes the staple holder and former mechanisms to return to their initial positions.

Uniquely, this mechanism also discloses a staple shape which allows for more secure alignment of this staple on the stapling surface. The staple is described with a notched shape in its crown. This notched shape mates with a similar notched shape formed on the staple holder so that the staple is automatically held and centered against the anvil. In this way, the staple is always secured, such that it is capable of being centered and applied uniformly each time the hernia repair mechanism is operated.

Furthermore, a stapler is disclosed which additionally contains an enhanced staple containing a pair of external notches. These notches provide a loading platform upon which the subsequent staples may be placed.

Finally, in the case of the multiple load mechanism, an improved lifter configuration is provided. This lifter mechanism contains a positive stopping surface in the portion of the staple cartridge upon which the staple lifter mechanism slides. This improvement creates reliable feeding and staple positioning.

These and other objects and descriptions and disclosures of the present invention will be more readily understood from the attached Detailed Description of the Drawings taken in connection with the Detailed Description of the Invention.

DETAILED DESCRIPTION OF THE DRAWINGS

FIGS. 1 and 1A are perspective final and assembly drawings respectively of the device of this invention;

FIG. 2 is a side elevation view of this invention;

FIGS. 3 and 3A are plan and elevation views of the fully retracted stapling mechanism;

FIGS. 4 and 4A are plan and elevation views of the stapling mechanism as the staple has begun to be formed;

FIGS. 5 and 5A are elevation and plan views of the staple as it is formed on the anvil of this invention;

FIGS. 6 and 6A are final positions of the staple as it is being ejected from the stapling mechanism;

FIG. 10 is a cross-sectional view of the multiple fire mechanism of FIG. 9;

FIG. 11 is a detailed cross-sectional view of the cartridge loading mechanism of this invention;

DETAILED DESCRIPTION OF THE INVENTION

Figure 7A:
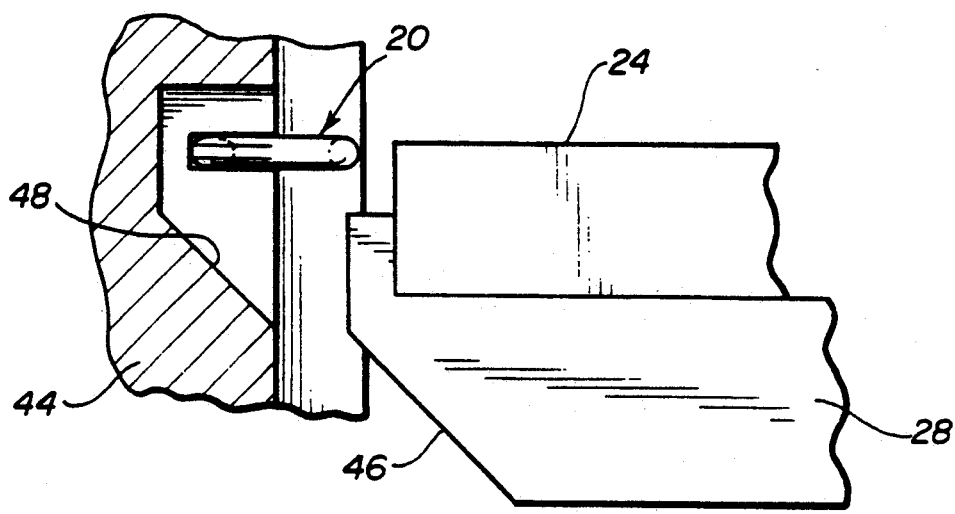
FIGS. 7A, 7B and 7C are plan views of the loading procedure of a single shot mechanism of this mechanism.

There is described in FIGS. 1, 1A and 2 an endoscopic hernia repair stapling mechanism 10 useful to apply mesh and prosthetics to herniated tissues or organs. This endoscopic mechanism is placed through a trocar cannula or tube, typically an Endopath TM Trocar manufactured by Ethicon, Inc., Somerville, N.J. 08876. The endoscopic portion 12 of the hernia repair mechanism 10 fits snugly within a cannula of a trocar, so that the procedure can take place within the cannula and in the abdominal cavity.

It is intended to use this device so that the stapler will apply a mesh around the herniated organ and then apply a staple either into the tissue or into the prosthetic mesh itself. Therefore, the stapling mechanism 10 must have some unique features. Preferentially, it is desirable to have a stapler which after the staples are formed does not need to be twisted to release the staples from the mechanism. This is true for a number of reasons. First, it is desirable to have a staple which comes off of the mechanism smoothly. Second, it is also desirable to have staple which will not tear tissue or inadvertently reposition the prosthetic which is applied over the herniated tissue, both while the staple is being applied and in removal, because the staple has been clinging to the stapler. Third, this feature of itself makes this type of stapler more reliable by more readily guaranteeing proper positioning and application of the staple by the user.

As seen in FIGS. 1 and 1A, there is described a trigger which is useful for firing the stapler. The trigger is connected to a driving mechanism which is capable of driving both the staple former and staple holder at the opposite end of the stapler. Also, this trigger mechanism is capable of advancing staples incrementally when they are loaded in a magazine type cartridge as is typically found in staplers of this sort. Finally, this trigger mechanism is capable of being used with a rotatable endoscopic portion, regardless of orientation of the stapling mechanism. A typical drive and rotatable mechanism can be found U.S. Ser. No. 479,318, filed Feb. 13, 1990 (SEN 58) which is herein incorporated by reference.

The trigger 14 and driving mechanism 16 of this invention actuate stapler mechanism 18 along the endoscopic portion 12 of the stapler. This driving mechanism 16 is capable of firing a staple 20 as is seen in FIGS. 3 through 6, and 3A through 6A. It is to be understood that, as is seen in FIGS. 1 and 2, that this driving mechanism 16 may be separated from the portion of the mechanism 10 containing trigger 14. This allows interchanging of sizes of staples 20, and cleaning of the driving portion 16 of the mechanism 10, if this is not a reusable device. Typically, attachment may occur at or near the screw portion 22 which allows rotation along the endoscopic portion of the mechanism.

Importantly, as seen in FIG. 1A, this device has a sheath 15, which is slightly larger in diameter than the stapler shaft 17. This sheath 15 is placed over the proximal end of the stapling mechanism during insertion into a trocar cannula and into the body cavity. Thereafter, a sliding mechanism (not shown) operates to slide sheath 15 distally over shaft 17.

As is seen in FIGS. 3 through 6 and FIGS. 3A through 6A, there is described in the drawings a method for both holding and firing staples 20. As is seen in FIG. 3 and 3A, the holder 24 is spring biased against the former 26.

As is better seen in conjunction with FIG. 2, former 26 extends along the length of the device, to be connected to driving mechanism 16. Compression spring 42 is attached at its proximal end to, and slides with former 26. Holder 24 is attached to spring 42 at the distal end of spring 42. The bias of spring 42 causes holder 24 to be initially placed adjacent stationary anvil 30. Movement of former 26 in a distal direction causes compression of spring 42 against holder 24.

Both the former 26 and the holder 24 are slidable in relationship to the stationary anvil 28. The stationary anvil 28 has at its end an anvil portion 30 around which the staple 20 may be formed. The staple holder 24 has a ledge 32 on which the crown 34 of the staple 20 may be seated. The staple holder 24, because it is biased by the former 26 in a position distal to the instrument, is able to maintain the staple 20 held against the anvil portion 20 at all times, until it is desired to eject the staple 20. This ejection occurs after the staple 20 has been formed.

Thus, as seen in these figures the staple 20 is initially positioned so that it is ready to engage either tissue or mesh wrapped around a herniated organ. The holder 24 securely maintains the crown 34 of staple 20 against the anvil portion 30, and the former 26 is retracted so that vision by the user of the staple 20 is not obscured when it is initially placed. (Of course, since this procedure is done through an endoscopic device, the viewing of the procedure must be done through a fiberoptic mechanism emplaced into the abdominal cavity through the cannula of a separate trocar device).

As is seen in FIGS. 4 and 4A, the holder 24 still maintains the staple crown 34 against the anvil portion 30, and now by squeezing the trigger 14 on the forming end 13 of the mechanism 10, the former 26 has begun to form the staple 20. The former legs 36 contacts the staple 20 at the end of the crown 34. These legs 36 of the former 26 entirely form the staple 20 about the anvil portion 30. As can be seen in FIG. 4A, the camming portion or camming means 38 of the former 26 placed underneath the staple holder 24 has moved to the camming portion or camming means 40 of the staple holder 24. In this way, the device is sequentially readying the staple 20 for ejection after forming.

As can be seen in FIGS. 5 and 5A, the staple 20 has now been entirely formed by the former 26. The former 26 is at its maximum position distally of the trigger 14. The staple 20 is entirely formed in a box shape and, if it has been secured on a prosthetic mesh covering a segment of herniated tissue, has entirely pierced and gripped the mesh. Of course, it is to be realized that the staple 20 can be placed into tissue so that the prosthetic mesh is permanently attached to be placed within the tissue.

As can be further seen in FIGS. 5 and 5A, the camming portion 38 of the former 26 has contacted the camming portion 40 of the staple holder 24. The former 26 has continued to be biased against the staple holder 24, so that the staple holder 24 holds the staple 20 against the anvil portion 30. Spring 42 which causes the biasing force is now fully compressed. With full compression, the staple holder 24 is now readying itself for ejecting the staple 20.

As can be seen in FIGS. 6 and 6A, the staple former 26 has now progressed so that the camming means 38 on the staple former 26 have fully contacted and cammed the camming means 40 on the staple holder 24. The staple holder 24 has been caused to be displaced laterally from the anvil 28. With such lateral displacement, the ledge 32 holding the staple against the anvil portion 30 has now moved to a position away from the anvil portion 30. The motion of ledge 32 causes staple 20 to be displaced from anvil 28. Therafter, retraction of former 26 causes the return of holder 24 to its original position, due to lack of engagement of the camming means 28, 40. As seen in FIG. 6A, when holder 24 returns to its position, staple 20 is now released from anvil 28, so that it may properly be placed in tissue and/or mesh as desired.

This unique staple forming sequence accomplishes full holding of staple 20 and full ejection without twisting or further emplacement of the staple 20, except that placement performed by the mechanism. This allows unique advantages to the user. For instance, the user is able to fully discern point of placement. He then retracts the stapler 10 after forming the staple knowing placement has been accomplished. This improvement allows the user also to focus on the point of placement with a fiber optic viewing mechanism and not worry about losing focus of the stapling site. Also, the user is now able to retract the mechanism 10 without worry of what adverse effects caused by twisting the mechanism away from the staple 20. These features all represent improvements over present devices.

Figure 9:
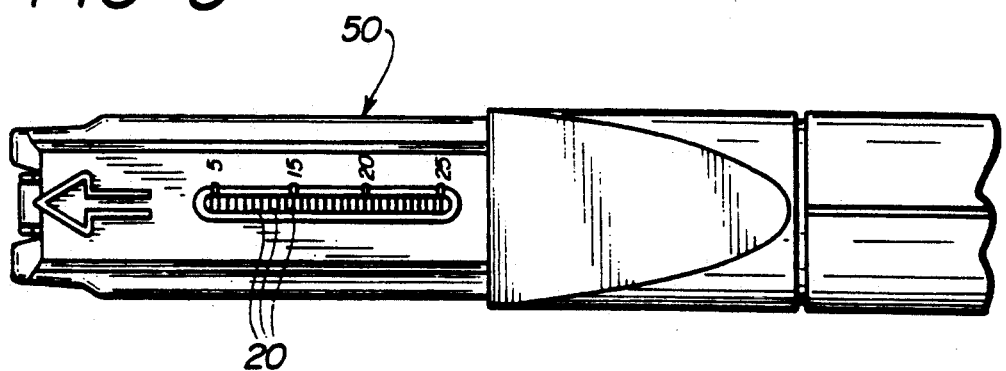
FIG. 9 is a plan view of a cartridge of staples useful for multiple firing mechanism using this invention.
Figure 11A:
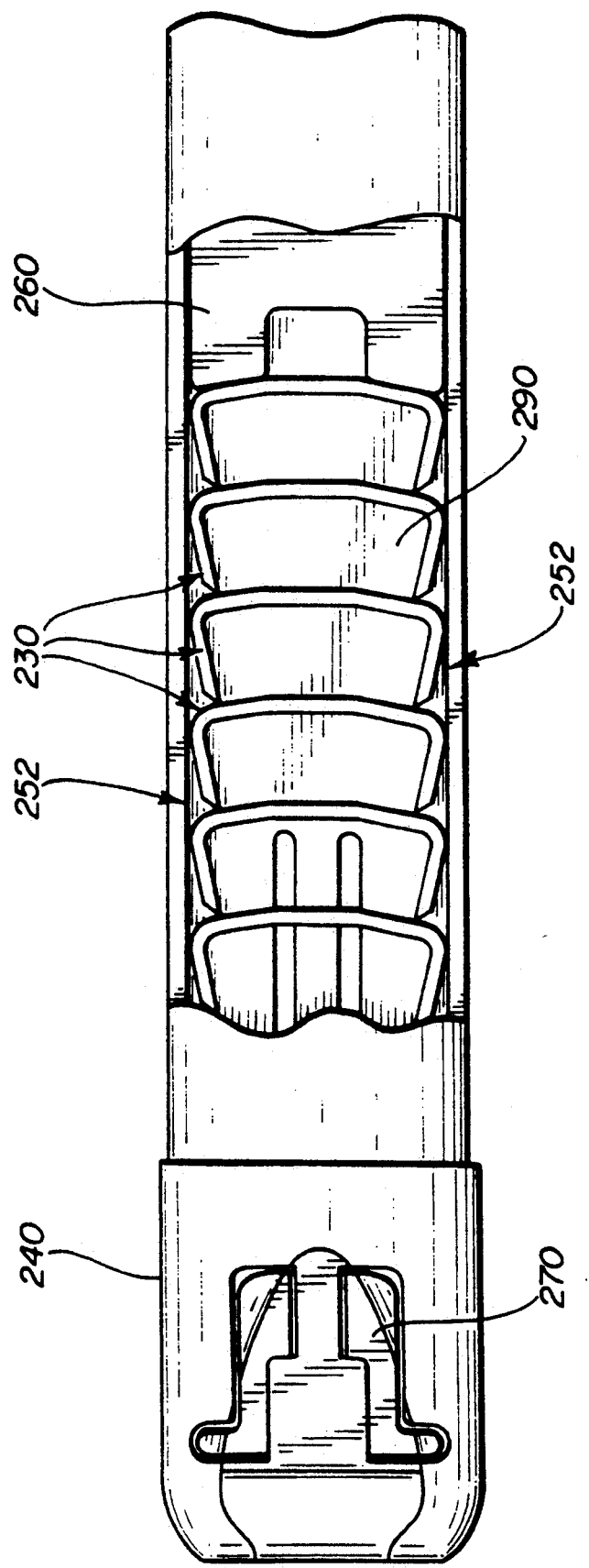
FIG. 11A is a cross-sectional view of the cartridge taken across lines 11A—11A of FIG. 11.
Figure 12:
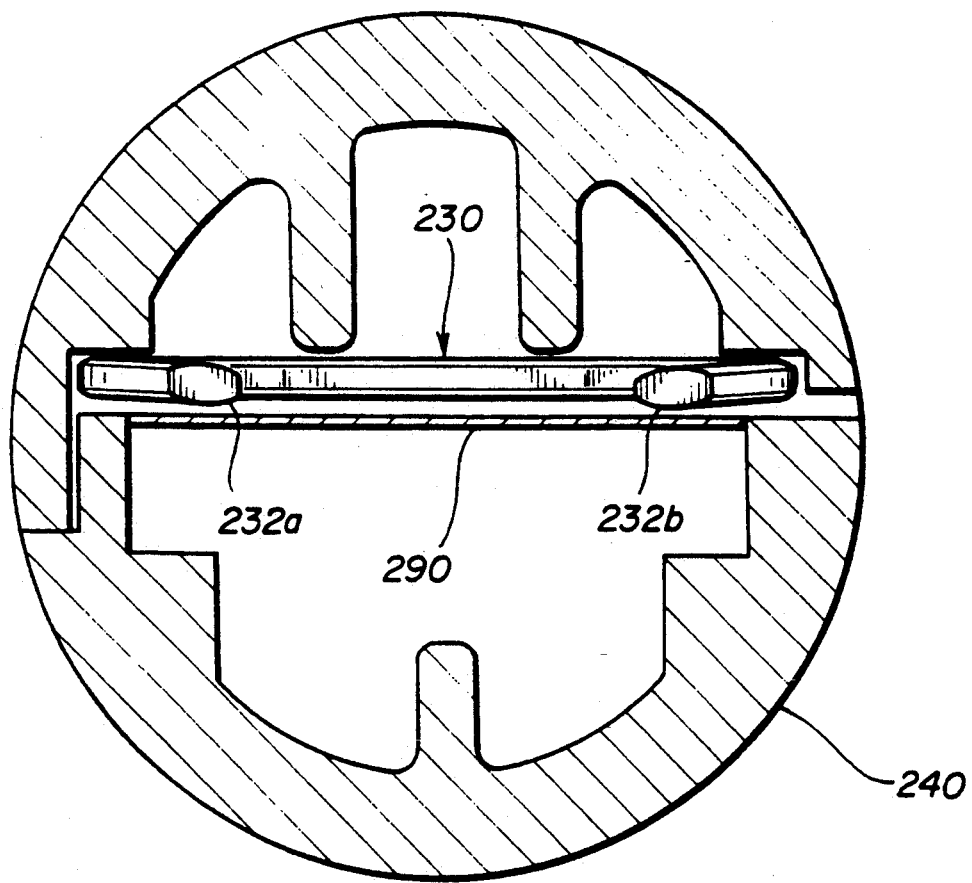
FIG. 12 is a cross-sectional view of the staple loading track as seen across line 12—12 of FIG. 11.

As can be seen from FIG. 9, there is disclosed a staple cartridge 50 much like the cartridge described in the previously referenced U.S. patent application Ser. No. 479,318. This cartridge 50 holds a number of staples 20. It sequentially advances the staples 50 by a spring mechanism. The staples 20 are moved into position, so that this alternate embodiment stapler may be considered a multiple fire device. As the trigger 14 is retracting so that the staple holder 24 and former 26 are returning to their original positions within the mechanism, the cartridge 50 as described in FIG. 9 is providing an additional staple 20 to the stapling site. A staple pick-off mechanism as described in the above referenced application may appropriately take the lead staple 20 in cartridge 50 and place it over staple former 26 and holder 24. A separate internal mechanism capable of retracting holder 24 proximally upon proximal movement of former 26 will need to activate holder 24 to create room for staple 20 between holder 24 and anvil portion 30. Then, staple 20 is placed on ledge 32, and all the loading mechanisms of the pick-off mechanism, which have placed staple 20 on ledge 32, retract into cartridge 50. Of course, because the staple holder 24 has appropriately been placed to hold the staple 20 in position, it is quite easy to begin a new firing function. Also, the next staple 20 in the cartridge 50 is ready for loading after the next firing sequence.

Figure 7B:
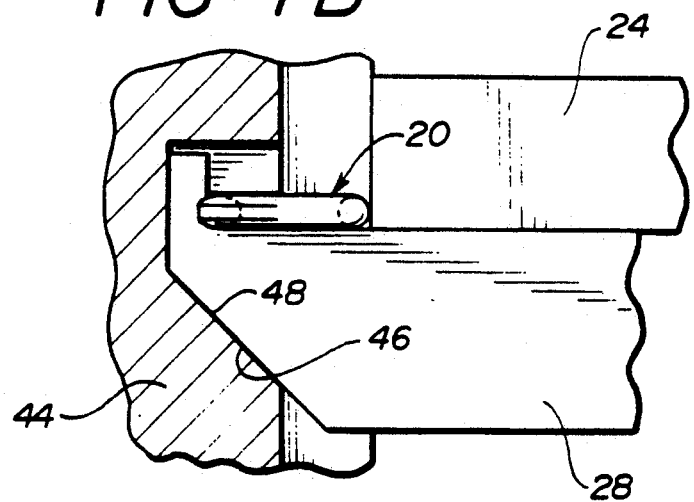
Figure 7C:
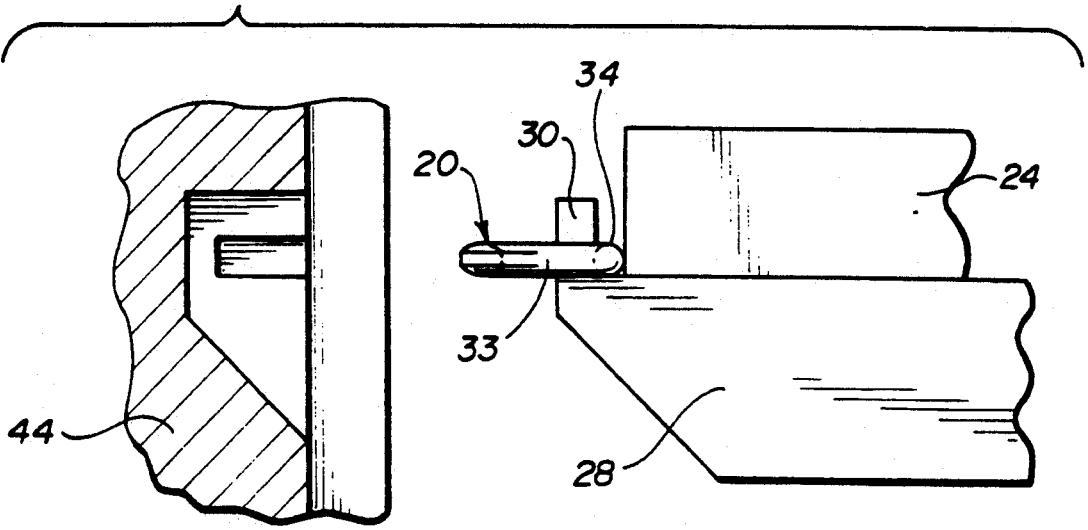

As seen in FIGS. 2, 7A, 7B and 7C as compared to the multiple fire sequence described above, in the described "single-shot" mechanism the staple 20 may be contained in an external cartridge 44 of staples. Generally these staples may number roughly 20 to the cartridge 44. A staple 20 is capable of being placed within the holder 24 as is seen in the Figures. As seen in FIG. 7A, the anvil 28 and holder 24 are advanced toward the staple 20 held within the cartridge 44. As seen in FIG. 7B, the anvil 28 has been fully placed into the cartridge so that the wedge shaped underside 46 of the anvil 28 matches wedge shaped portion 48 of the cartridge 44. Now, the spring biasing force exerted by the former 26 against the holder 24 by spring 42 has been overcome so that the holder 24 is pushed proximally towards trigger 14. When this occurs, room is made between the anvil 28 and legs 32 of the holder 24 so that the crown 30 of the staple 20 may be placed on the holder ledge 32. As can be better seen in FIG. 7C, the crown 34 is wedged between the holder 24 and the anvil portion 30. Thus, the crown 34 of the staple 20 is seated on the holder ledge 32, and is securely held tightly by the biased holder 24 and the anvil 28. The mechanism 10 is removed from the cartridge 44 so that the staple 20 is removed from its moorings in the cartridge 44. The anvil portion 30 forces the staple crown 34 and ultimately the staple legs 33 out of the cartridge 44, and the staple 20 is held securely within the stapling device 10.

Figure 8A:
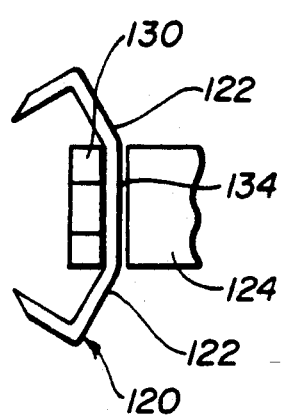
FIGS. 8A, 8B and 8C are plan views of possible stapler configurations of this invention, including a novel alignment feature for these staples.

Of course, it is to be realized that any of these mechanisms securely hold and fire such staples. However, it is further desirable to have a proper alignment mechanism to hold the staples in place. Some such alignment mechanisms are described in FIGS. 8A, 8B, and 8C. As is seen in FIG. 8A, a staple 120 is placed between holder 124 and anvil 130. The preformed hexagonally shaped staples 120 are formed so that the legs 122 formed around the crown 134 self-center the Whole staple 120 on anvil 130.

Figure 8B:
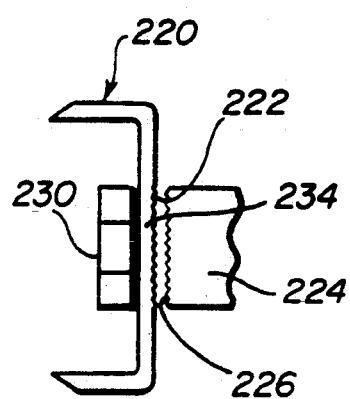

Alternately, as in FIG. 8B, a staple 220 may be formed with serrations 222 on one of the sides of crown 234. The serrations 222 mesh with serrations 226 on holder 224. Alternately, anvil 230 may have serrations 234, so that there is even more secure placement and centering of staple 220 holder, and against the anvil 234.

Figure 8C:
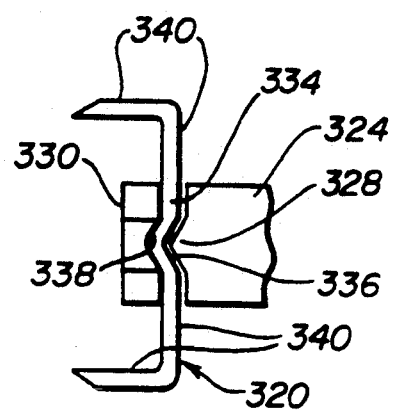

Finally, as seen in FIG. 8C, there is created a notch 336 to the staple crown 334. This notch 336 fits against the anvil 330 at a notch 336 at a notch 338 made in anvil 330. Furthermore, a notch 328 is made in holder 324. These notches 328, 336, 338 maintain triple alignment of the staple 320 held within the holder 324 and anvil 330. The user is assured that staple 320 will form with equal size legs 340 on either side of the stapler former. A box formed staple shape is assured.

In use the mechanism 10 of this invention is created so that it grasps a staple 20 between the staple holder 24 and anvil 28. This can either be done from a external cartridge 44 of staples 20 or a magazine 50 of staples within the mechanism 10. Of course, the endoscopic portion 12 of the stapler has been attached to the driving mechanism 16 and trigger 14. The endoscopic portion 12 may be rotatable if so desired. Once a proper place has been derived for staple 20 emplacement, the endoscopic portion 12 is locked in place so that placement can be assured.

Trigger 14 is fired and the unique holding and ejecting mechanism allows the staple 20 to be held, formed and ejected in a repeatable and assurable manner. Also, once the staple 20 has been formed, ejection is accomplished without twisting or any other function, other than retraction of the repair device 10 from the staple site. Because the stale 20 is formed in a box shape, it is found useful to apply to tissue and mesh prosthetics held around the tissue, or mesh prosthetics covering herniated tissue. In this fashion, the mechanism 10 applying staple 20 is able to hold the mesh in place permanently, or until healing occurs.

As seen in FIGS. 10-16, there is described an alternate embodiment of a multiple fire mechanism 150 performing similarly with the cartridge 50 described in FIG. 9 and above. The configuration of this stapler 150 obviates the need for a staple holder as in the single-fire device. Rather, a staple feeder and driver combination control the position of the staples throughout the firing, as will be explained further herein. The handle 200 containing an actuator mechanism 220 operates identically to those described in Ser. No. 479,318. This actuator mechanism operates to cause a drive 210 to operate within the cartridge portion 240 which can also be considered the endoscopic portion of the instrument of the mechanism. As in Ser. No. 479,318, the cartridge 240 is able to rotate about actuator 220 and handle 200 of this instrument 150. Also, driver 210 is able to be oriented in any position for firing. Naturally, it is cartridge 240 which is circular in shape and capable of fitting in the cannula of a surgical trocar, like the 10-11 mm Endopath TM Trocar marketed by Ethicon, Inc., Somerville, N.J. 08876.

As seen in FIGS. 11, 13, 14 and 15, there are a plurality of staples 230 located in cartridge 240. Staple 230 contains a pair of legs 232 separated by a proximal portion or crown 234. These staples 230 are generally at least twelve in number, lie flat along the longitudinal axis of cartridge 240, and are positively urged toward the distal end of cartridge 240 near the anvil 250. Cartridge 240 may ideally be rotatable about handle 200.

This new endoscopic staple 230 has been developed with a notch 236 in each of the sides adjacent legs 232 in the proximal portion 234 of the staple 230. With this design, the points 232a, 232b of the following or next sequential staple 230 rest in the notches 236 of the 15 preceding staple 230, and each of these staples 230 can be constrained to match the motions of the lead staple. In this way, notches 236 on a distal staple control relation of the legs 232a, 232b on a proximal staple. With a number of notched staples 230 lined in a stack and constrained by staple track 252, the stack acts as a single long member which is difficult to rotate. The staples 230 therefore feed in line without rotating in track 252 and are consequently, less likely to jam.

As seen in FIGS. 11A, 12, 15 and 16, this stapling mechanism 150 contains a firing system similar to that of Ser. No. 479,318, and that of the single fire mechanism 10 described above. There is contained in cartridge 240, a driver 210 which causes staples 230 to be formed. Feeder 260 enables a first staple 230 to be placed in position for firing. Lifter 270 takes the forwardmost of staples 230 from stack 252 to be placed in the path of driver 210, in order to be formed. Ejector 280 in the form of a leaf spring placed along the axis of cartridge 240, is capable of moving transverse this axis so that it kicks formed staples from the mechanism 150.

Figure 13:
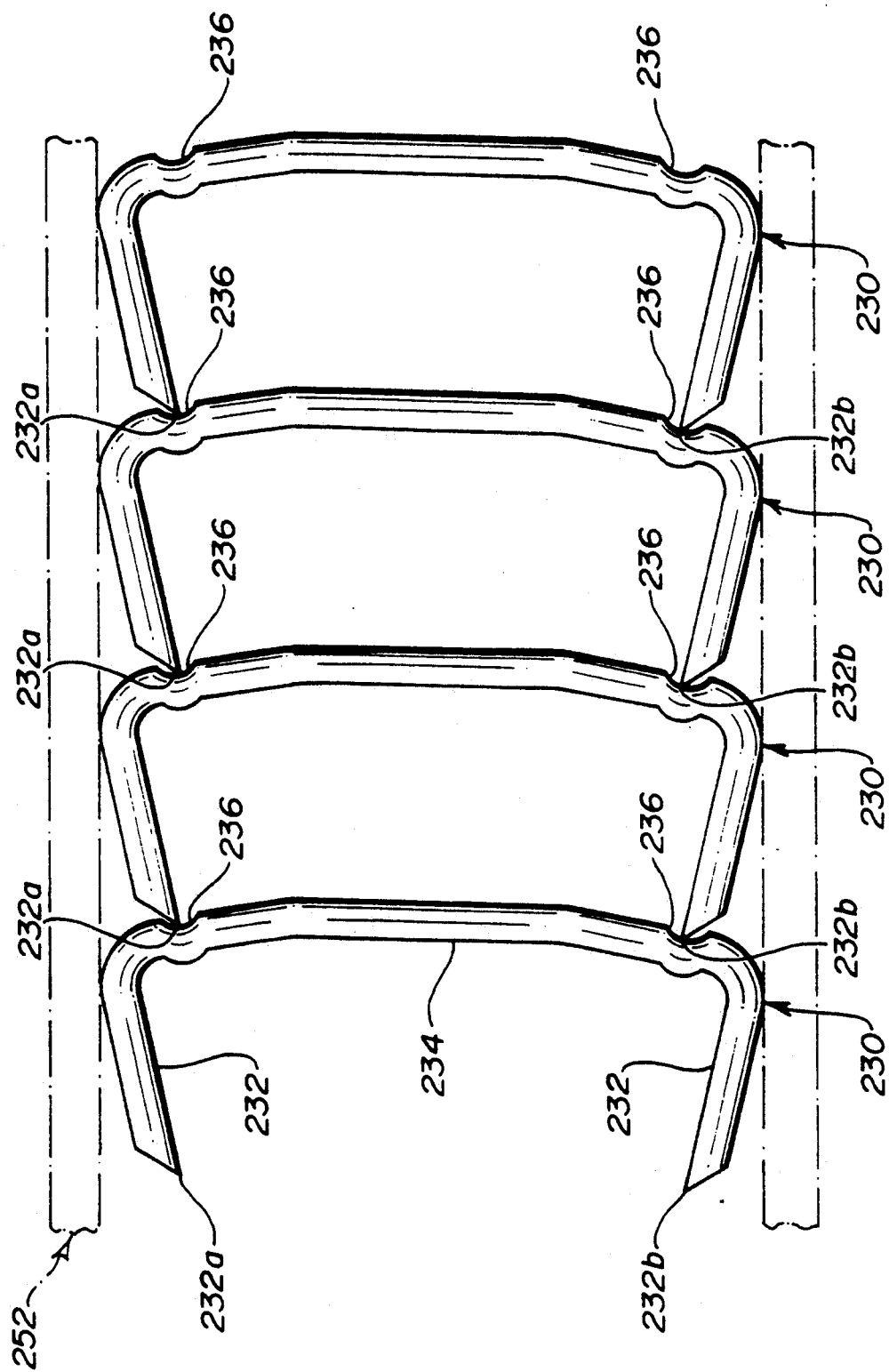
FIG. 13 is a plan view of a new configuration staple held in the staple stack used in this mechanism.
Figure 14:
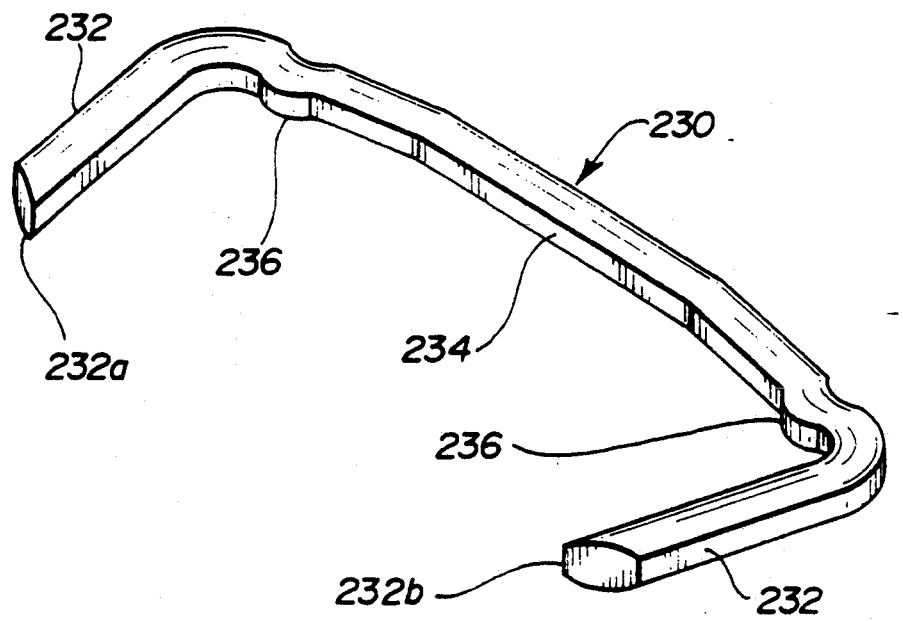
FIG. 14 is a perspective view of a single staple as seen in FIG. 13.

Firing staples 230 from the device 150 occurs as described below, starting with a staple formation stroke just completed. With the trigger 220 fully engaged, the driver 210 rests against the formed staple 230, which in turn rests against the anvil 250. In this state the staple 230 is ready to be kicked off by ejector 280 which acts as a leaf spring. Lifter 270 is in its fully forward position, having operated to place the forwardmost staple 230 in the path of driver 230 to be formed at anvil 250. With the lifter 270 positioned in this manner, a staple 230 has been fed by the feeder 260 behind the stack of horizontally loaded staples 230 (FIG. 13). Since the staple track 252 in the cartridge 240 supports the staple 230 on its way to the lifter 270, a rearward staple 230 cannot rotate or ride over a staple 230 in front of it. Once positioned beneath lifter 270 the staple 230 is not held within track 252 any longer, but is supported between staple plate 290 (FIG. 15), the stops 300 and the lifter 270 underside.

As the firing process continues, the driver 210 is retracted by releasing the trigger 220 of the handle 200; the ejector spring 280 kicks off the previously formed staple 230 since the staple is no longer held fast against the anvil 250 by the driver 210. At the same time the lifter 270, forced by a spring 274 which acts as a coil spring, but restrained by the surface of driver 210, starts to drop the next staple 230 to be formed into place in front of the driver 210. Meanwhile, the feeder 260 is forcing the stack of staples toward the lifter 270, with the lead staple 230 restrained from double feeding by the back 271 of the lifter 270 which, provides a stopping surface for the inside of the of the staple crown 234. Once the driver 210 is pulled back fully by releasing the trigger, the staple 230 is positioned (by the now fully depressed lifter 270) in front of the driver 210 for firing. As the trigger 220 is pulled, the driver 210 moves forward, forces the lifter 270 and staple plate 290 out of its way while engaging the staple 230, along legs 232, and, as well, crown 234 on formation of the stapler 230. Moving the staple 230 forward leads to final formation around the anvil 250. During these final stages of staple fire, the lifter 270 and staple plate 290 are simultaneously forced aside by the driver 210 such that the feeder 230 can force the staple stack 252 forward to put in place the next staple for firing, positioned below the lifter 270.

Figure 15:
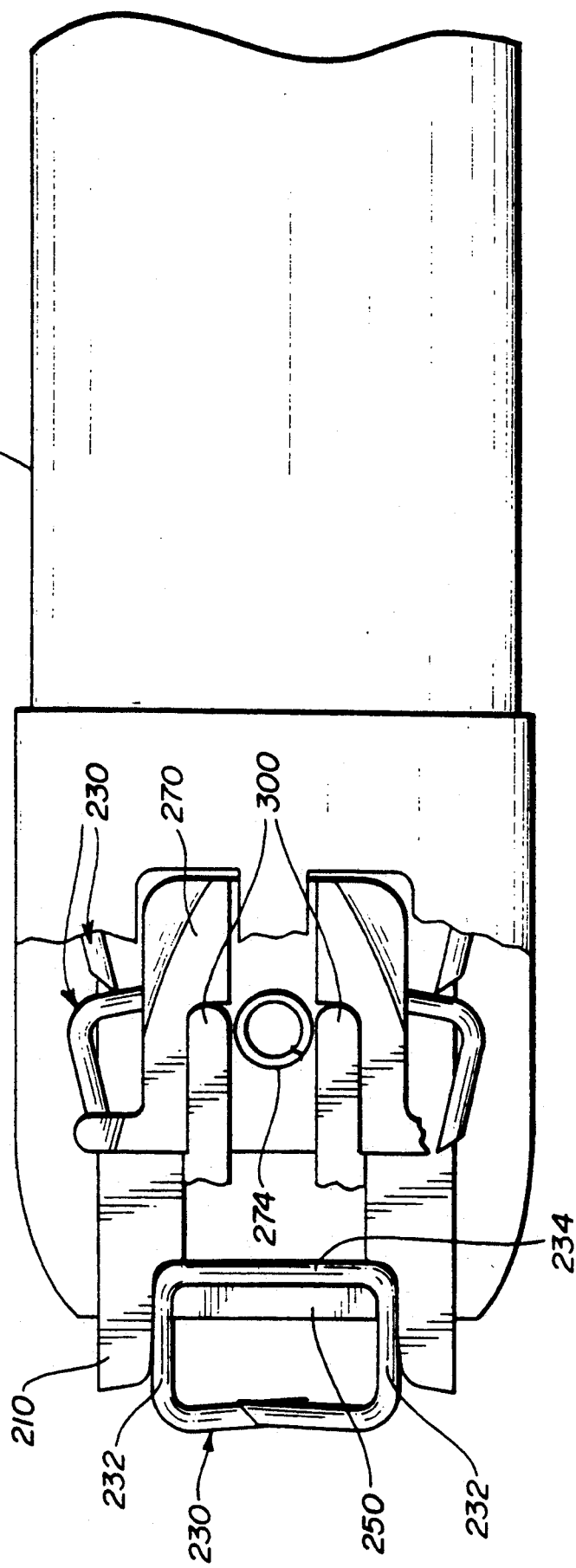
FIG. 15 is an cross-sectional view of the staple stack of FIG. 11, as taken across lines 15—15.
Figure 16:
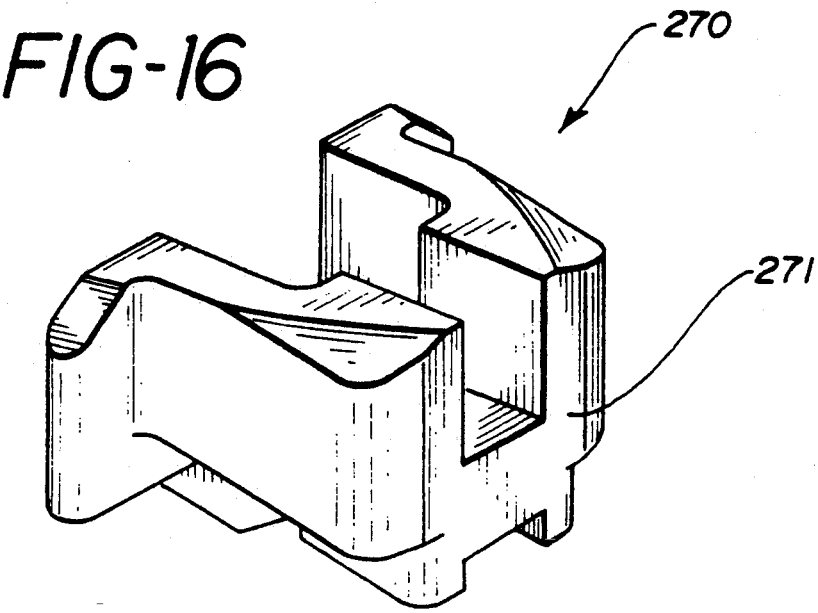
FIG. 16 is a perspective view of the improved staple lifter of this invention.
Figure 17:
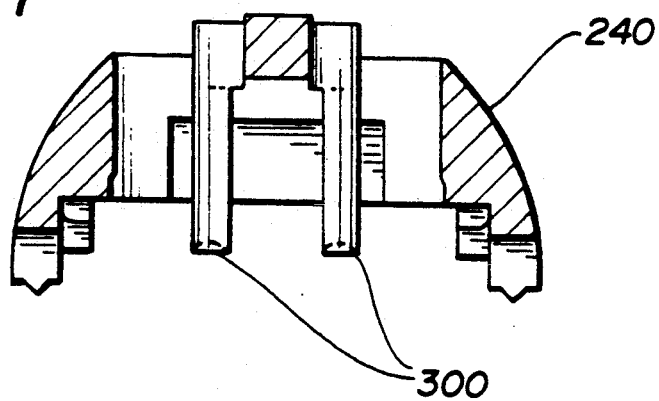
FIG. 17 is an underside view of an embodiment of the stapler cartridge of this invention.

As can be seen in FIGS. 15, 16 and 17, rather than rely on the lifter surface features 270 to provide the stopping action required for a staple 230 to be positioned, positive stops 300 were developed in the upper portion of cartridge 240 about which the lifter fits and slides. With this design there is no reliance on the lifter 270 itself to keep the staple 230 from moving further forward as it is being forced out of the plane of staple stack 252 and into the path of driver 210. Prevention of staple double feeding and rotation is significantly improved. The lifter 270 is now called on to only drop the staple into place. In addition, the increased track surfaces provide greater constraints on the undesired motions of the lifter 270.

As can be further seen from FIGS. 10 and 17, the lifter 270 can only be pushed up by the driver 210 if there is a staple ready for fire located beneath it. With the last staple fired, the lifter 270 falls to a position where the driver 210 contacts a perpendicular rear surface 271 on lifter 270 rather than a more typical angled surface. This surface 271 is the same surface which prevents double feeding of staples 230 from stack 252 into the path of driver 210. As the driver 210 does not have a sloped surface at this contact point, the driver is positively stopped. Since the driver 210 is stopped at a point before that normally associated with a complete staple firing, the fact that a cartridge 240 is empty will be evident to the surgeon.

The invention has been described in connection w a particularly preferred embodiment. However, it is to be understood that it is only the claims of the invention and their equivalents which are meant to describe this invention.

What is claimed is:

1. A stapling mechanism comprising:
   a firing mechanism capable of moving along a longitudinal path defining a longitudinal axis;
   a staple closing mechanism attached to said firing mechanism, said closing mechanism capable of closing staples;
   a cartridge attached to said firing mechanism and said cartridge placed along said longitudinal axis and containing said firing mechanism; and
   said cartridge containing a stack of staples arranged from a distalmost staple closest said staple closing mechanism to a proximal staple, each of said staples comprising a crown with a tissue facing distal side and a proximal side, and having two ends;
   each said crown end having a notch, said notch comprising an indentation in said crown toward said distal side and away form said proximal side; and
   a pair of legs, each leg attached to said notch and extending therefrom, and each leg having a sharpened distal end and said staples arranged such that each of said staples lie along said axis with the leg distal ends of a proximal staple contacting the corresponding crown notches of an adjacent distal staple; and
   a transfer mechanism engageable with said firing mechanism and capable of transferring a staple from said staple stack and into said path, and comprising a lifter positioned in said cartridge and moveable transverse to said longitudinal axis, said lifter having a sloped surface, and the distalmost staple in said stack engageable with said sloped surface to move from said stack and into said path; and wherein
   said cartridge is circular and is capable of being placed in a trocar tube 10 mm in diameter.

2. The stapler of claim 1 wherein said staple stack is contained in a track formed within said cartridge and said staples are constrained in said stack by a planar face on said lifter, and said cartridge further including a driver formed as part of said firing mechanism and engageable with the forwardmost staple on said stack engaged with said planar face on said lifter, such that said driver is capable of stripping said staple from said lifter, moving said stale along said sloped surface, and positioning said staple into the path of said firing mechanism.

3. The staple of claim 2 further including a stop means on said lifter, said stop means engageable with said driver when there are no longer any staples loaded in said cartridge.

4. The stapling mechanism of claim 1 further defined as an endoscopic stapling mechanism, containing an endoscopic portion, said endoscopic portion containing said cartridge, said firing mechanism and said transfer mechanism;
   and said stapling mechanism containing an actuating mechanism attached to said firing mechanism.

5. The stapler of claim 4 wherein said cartridge is rotatable about said longitudinal axis.

6. The stapler of claim 5 wherein said actuating mechanism is a trigger.

7. An endoscopic cartridge comprising:
   a firing mechanism capable of moving along a longitudinal path and defining a longitudinal axis and containing a driver and an anvil;
   a stack of staples placed along said longitudinal axis;
   a transfer mechanism engageable with said firing mechanism and capable of transferring a staple from said staple stack and into said path, and comprising a lifter positioned in said cartridge and moveable transverse to said longitudinal axis, said lifter having a sloped surface, and the distalmost staple in said stack engageable with said sloped surface to move from said stack and into said path; and wherein
   said cartridge is circular and is capable of being placed in a trocar tube 10 mm in diameter.

8. The cartridge of claim 7 further comprising a planar face on said lifter, such that said driver is engageable with the forwardmost staple on said stack engaged with said planar face on said lifter, such that said driver is capable of stripping said staple from said lifter, moving said staple along said sloped surface, and positioning said staple on said anvil for forming.

9. The cartridge of claim 8 further including a stop means on said lifter, said stop means engageable with said driver when there are no longer any staples loaded in said cartridge.

10. A surgical stapler comprising the cartridge of claim 7 and further containing an actuating mechanism attached to said cartridge.

11. The stapler of claim 10 wherein said actuating mechanism is a trigger.

12. The stapler of claim 10 wherein said cartridge is rotatable about said longitudinal axis.

13. The cartridge of claim 7 wherein the staples of said stack are arranged such that each said staple contains a crown with a tissue facing distal side and a proximal side, and having two ends;

each said crown having a notch, said notch comprising an indentation in said crown toward said distal side and away from said proximal side; and a pair of legs, each leg attached to said notch and extending therefrom, and each leg having a sharpened distal end;

and said staples arranged such that each of said staples lie along said axis with the leg distal ends of a proximal staple contacting the notches of an adjacent distal staple.

* * * * *